US011382568B2

(12) United States Patent
Katsuki et al.

(10) Patent No.: US 11,382,568 B2
(45) Date of Patent: *Jul. 12, 2022

(54) OBTAINMENT OF CLEANED SEQUENCES RELATING TO A CENTER OF GRAVITY

(71) Applicant: INTERNATIONAL BUSINESS MACHINES CORPORATION, Armonk, NY (US)

(72) Inventors: Takayuki Katsuki, Tokyo (JP); Tetsuro Morimura, Tokyo (JP)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 333 days.

This patent is subject to a terminal disclaimer.

(21) Appl. No.: 16/654,138

(22) Filed: Oct. 16, 2019

(65) Prior Publication Data

US 2020/0046297 A1 Feb. 13, 2020

Related U.S. Application Data

(63) Continuation of application No. 15/076,078, filed on Mar. 21, 2016, now Pat. No. 10,602,988.

(51) Int. Cl.
*A61B 5/00* (2006.01)
*A61B 5/11* (2006.01)
(Continued)

(52) U.S. Cl.
CPC .............. *A61B 5/7203* (2013.01); *A61B 5/02* (2013.01); *A61B 5/08* (2013.01); *A61B 5/113* (2013.01);
(Continued)

(58) Field of Classification Search
CPC ... A61B 5/6891; A61B 5/6892; A61B 5/7203; A61B 5/1102; A61B 5/1128;
(Continued)

(56) References Cited

U.S. PATENT DOCUMENTS 6,840,907 B1 1/2005 Brydon
8,734,360 B2 5/2014 Klap et al.
(Continued)

OTHER PUBLICATIONS

List of IBM Patents or Patent Applications Treated as Related dated Oct. 16, 2019, 2 pages.
Beattie, Z. et al., "Classification of Breathing Events Using Load Cells under the Bed" Annual International Conference of the Engineering in Medicine and Biology Society, Sep. 2009. (pp. 1-9).
(Continued)

*Primary Examiner* — Christian Jang
*Assistant Examiner* — Anna Roberts
(74) *Attorney, Agent, or Firm* — Tutunjian & Bitetto, P.C.; Randall Bluestone

(57) ABSTRACT

Methods and systems are provided for obtaining cleaned sequences showing trajectories of movement of a center of gravity and for estimating a biometric information pattern or value of a target. One of the methods includes removing noises from initial sequences showing trajectories of movement of a center of gravity to obtain the cleaned sequences. Another one of the methods includes reading cleaned sequences of the target into a memory, extracting features from the cleaned sequences, and estimating a biometric information pattern or value of the target from the extracted features, using a classification or regression model of biometric information patterns or values. The biometric information pattern may be a pattern derived from respiratory or circulatory organs of a target.

20 Claims, 9 Drawing Sheets

(51) Int. Cl.
*A61B 5/113* (2006.01)
*A61B 5/02* (2006.01)
*A61B 5/08* (2006.01)

(52) U.S. Cl.
CPC .......... *A61B 5/1122* (2013.01); *A61B 5/1128* (2013.01); *A61B 5/6891* (2013.01); *A61B 5/6892* (2013.01); *A61B 5/7267* (2013.01); *A61B 5/7275* (2013.01); *A61B 5/1102* (2013.01); *A61B 2560/0223* (2013.01); *A61B 2560/0475* (2013.01); *A61B 2562/0252* (2013.01); *A61B 2562/043* (2013.01)

(58) Field of Classification Search
CPC ............ A61B 5/113; A61B 2560/0223; A61B 2560/0475; A61B 2562/0252; A61B 2562/043; A61B 5/7275; A61B 5/1122
USPC .......................................................... 700/191
See application file for complete search history.

(56) References Cited

U.S. PATENT DOCUMENTS

| | | | |
|---|---|---|---|
| 8,905,928 B2 | 12/2014 | Hayes et al. | |
| 8,972,197 B2 | 3/2015 | Jangle et al. | |
| 9,108,009 B2 | 8/2015 | Rapoport et al. | |
| 9,202,102 B1* | 12/2015 | Sahin .................... | G06K 9/3208 |
| 2008/0005838 A1* | 1/2008 | Wan Fong ........... | A61B 5/4094 |
| | | | 5/600 |
| 2014/0276242 A1 | 9/2014 | Chen et al. | |
| 2015/0094606 A1 | 4/2015 | Mestha et al. | |
| 2017/0326412 A1 | 11/2017 | Scholl et al. | |

OTHER PUBLICATIONS

Mccaughey, E. et al., "Non-Intrusive Real-Time Breathing Pattern Detection And Classification For Automatic Abdominal Functional Electrical Stimulation" Medical Engineering & Physics, vol. 36, Jun. 2014. (pp. 1-6).

* cited by examiner

OBTAINMENT OF CLEANED SEQUENCES RELATING TO A CENTER OF GRAVITY

BACKGROUND

Technical Field

This invention relates to an obtainment of cleaned sequences showing trajectories of movement of a center of gravity. Further, this invention relates to an estimation of a biometric information pattern or value of a target, using the cleaned sequences mentioned above.

Description of the Related Art

In healthcare scenarios, visual-sign monitoring is an important aspect of all medical problems and treatments. Accordingly, it is necessary to monitor a biometric information pattern of a target, such as a respiration pattern or a heart beat pattern.

Most of the methods used in practice today are somewhat constrained and/or invasive to the patient or a person who needs nursing care.

In general, respiration patterns are obtained from intrusive sensors, such as sensors attaching over nose. These intrusive sensors cause a burden to patients in many cases.

SUMMARY

According to one aspect of an embodiment of the present invention, a computer-implemented method for obtaining cleaned sequences showing trajectories of movement of a center of gravity is provided. The method comprises the following step: removing one or more noises from one or more initial sequences showing one or more trajectories of movement of a center of gravity to obtain the cleaned sequences.

According to another aspect of an embodiment of the present invention, a computer-implemented method for estimating a biometric information pattern or value of a target is provided. The method comprises the following step: reading cleaned sequences of the target into a memory; extracting features from the cleaned sequences; and estimating a biometric information pattern or value of the target from the extracted features, using a classification or regression model of biometric information patterns or values.

According to another aspect of the present invention, a system comprising a computer readable storage medium storing a program of instructions executable by the computer system to perform one or more methods described herein may be provided.

According to another aspect of the present invention, a computer program product comprising a computer readable storage medium storing a program of instructions executable by the computer system to perform one or more methods described herein also may be provided.

DETAILED DESCRIPTION

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

To define more clearly the terms used herein, the exemplified definitions are provided herein, but the meaning of the terms should be interpreted broadly as known to the technical field to which the present invention relates.

Figure 1:
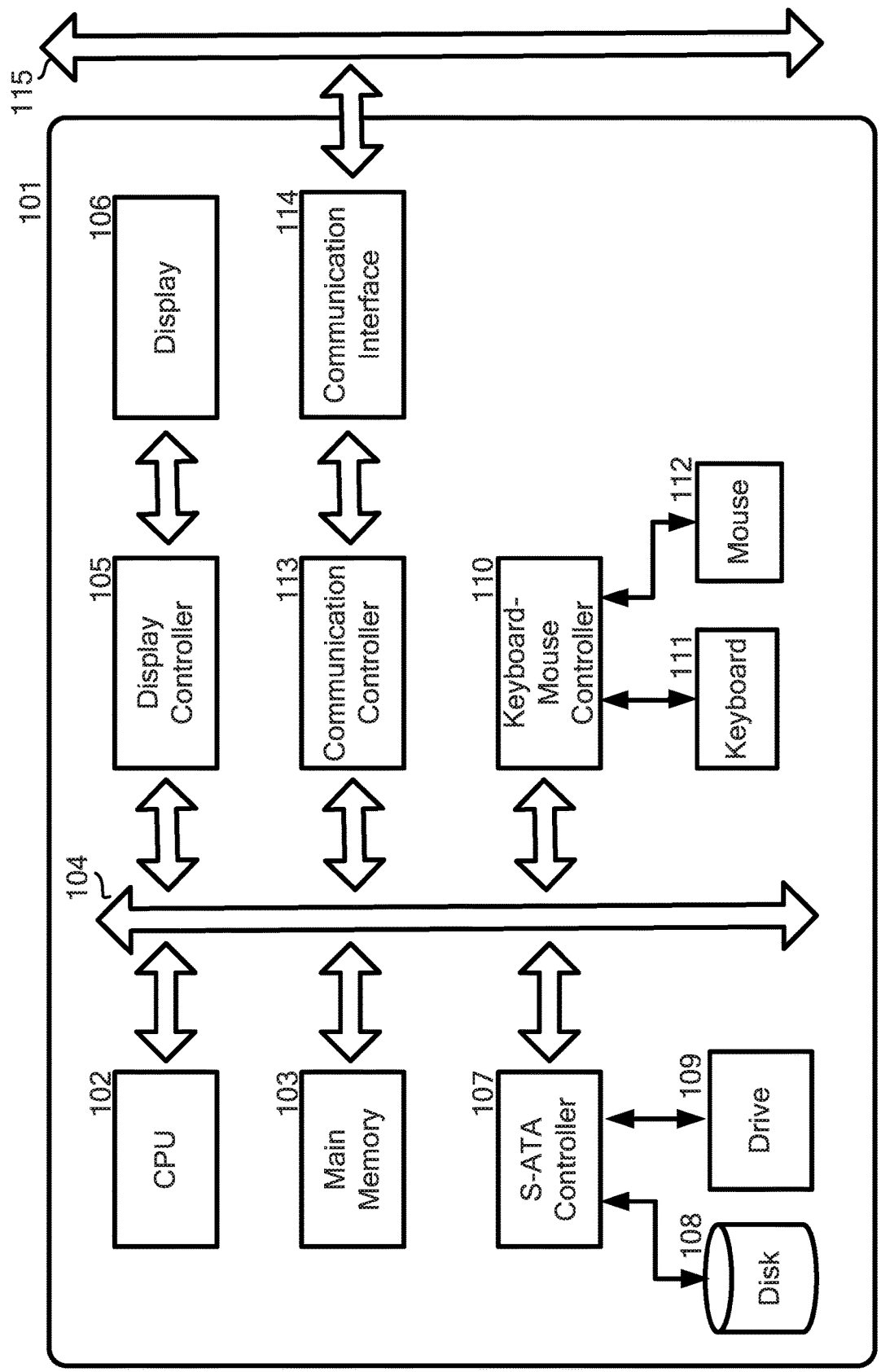
FIG. 1 illustrates an exemplified basic block diagram of a device used in an embodiment of the present invention.

With reference now to FIG. 1, FIG. 1 illustrates an exemplified basic block diagram of computer hardware used in an embodiment of the present invention.

A computer (101) may be, for example, but is not limited to, a desktop, a laptop, a notebook, a tablet or a server computer. The server computer may be, for example, but is not limited to, a workstation, a rack-mount type server, a blade type server, or a mainframe server and may run, for example, a hypervisor for creating and running one or more virtual machines. The computer (101) may comprise one or more CPUs (102) and a main memory (103) connected to a bus (104). The CPU (102) may be preferably based on a 32-bit or 64-bit architecture. The CPU (102) may be, for example, but is not limited to, the Power® series of International Business Machines Corporation; the Core i™ series, the Core 2™ series, the Atom™ series, the Xeon™ series, the Pentium® series, or the Celeron® series of Intel Corporation; or the Phenom™ series, the Athlon™ series, the Turion™ series, or Sempron™ of Advanced Micro Devices, Inc. ("Power" is registered trademark of International Business Machines Corporation in the United States, other countries, or both; "Core i", "Core 2", "Atom", and "Xeon" are trademarks, and "Pentium" and "Celeron" are registered trademarks of Intel Corporation in the United States, other countries, or both; "Phenom", "Athlon", "Turion", and "Sempron" are trademarks of Advanced Micro Devices, Inc. in the United States, other countries, or both).

A display (106) such as a liquid crystal display (LCD) may be connected to the bus (104) via a display controller (105). The display (106) may be used to display, for management of the computer(s), information on a computer connected to a network via a communication line and information on software running on the computer using an appropriate graphics interface. A disk (108) such as a hard disk or a solid state drive, SSD, and a drive (109) such as a CD, a DVD, or a BD (Blu-ray disk) drive may be connected to the bus (104) via an SATA or IDE controller (107). Moreover, a keyboard (111) and a mouse (112) may be connected to the bus (104) via a keyboard-mouse controller (110) or USB bus (not shown).

An operating system, programs providing Windows®, UNIX® Mac OS®, Linux®, or a Java® processing environment, Java® applications, a Java® virtual machine (VM), and a Java® just-in-time (JIT) compiler, such as J2EE®, other programs, and any data may be stored in the disk (108) to be loadable to the main memory. ("Windows" is a registered trademark of Microsoft corporation in the United States, other countries, or both; "UNIX" is a registered trademark of the Open Group in the United States, other countries, or both; "Mac OS" is a registered trademark of Apple Inc. in the United States, other countries, or both; "Linux" is a registered trademark of Linus Torvalds in the United States, other countries, or both; and "Java" and "J2EE" are registered trademarks of Oracle America, Inc. in the United States, other countries, or both).

The drive (109) may be used to install a program, such as the computer program of an embodiment of the present invention, readable from a CD-ROM, a DVD-ROM, or a BD to the disk (108) or to load any data readable from a CD-ROM, a DVD-ROM, or a BD into the main memory (103) or the disk (108), if necessary.

A communication interface (114) may be based on, for example, but is not limited to, the Ethernet® protocol. The communication interface (114) may be connected to the bus (104) via a communication controller (113), physically connects the computer (101) to a communication line (115), and may provide a network interface layer to the TCP/IP communication protocol of a communication function of the operating system of the computer (101). In this case, the communication line (115) may be a wired LAN environment or a wireless LAN environment based on wireless LAN connectivity standards, for example, but is not limited to, IEEE® 802.11a/b/g/n ("IEEE" is a registered trademark of Institute of Electrical and Electronics Engineers, Inc. in the United States, other countries, or both).

Hereinafter, an embodiment of the present invention will be described with reference to the following: FIG. 2, FIGS. 3A to 3C, FIG. 4, and FIGS. 5A to 5C.

The idea of an embodiment of the present invention is on the basis that load sensors attached to a bed or chair is promising for non-intrusive sensing.

Figure 2A:
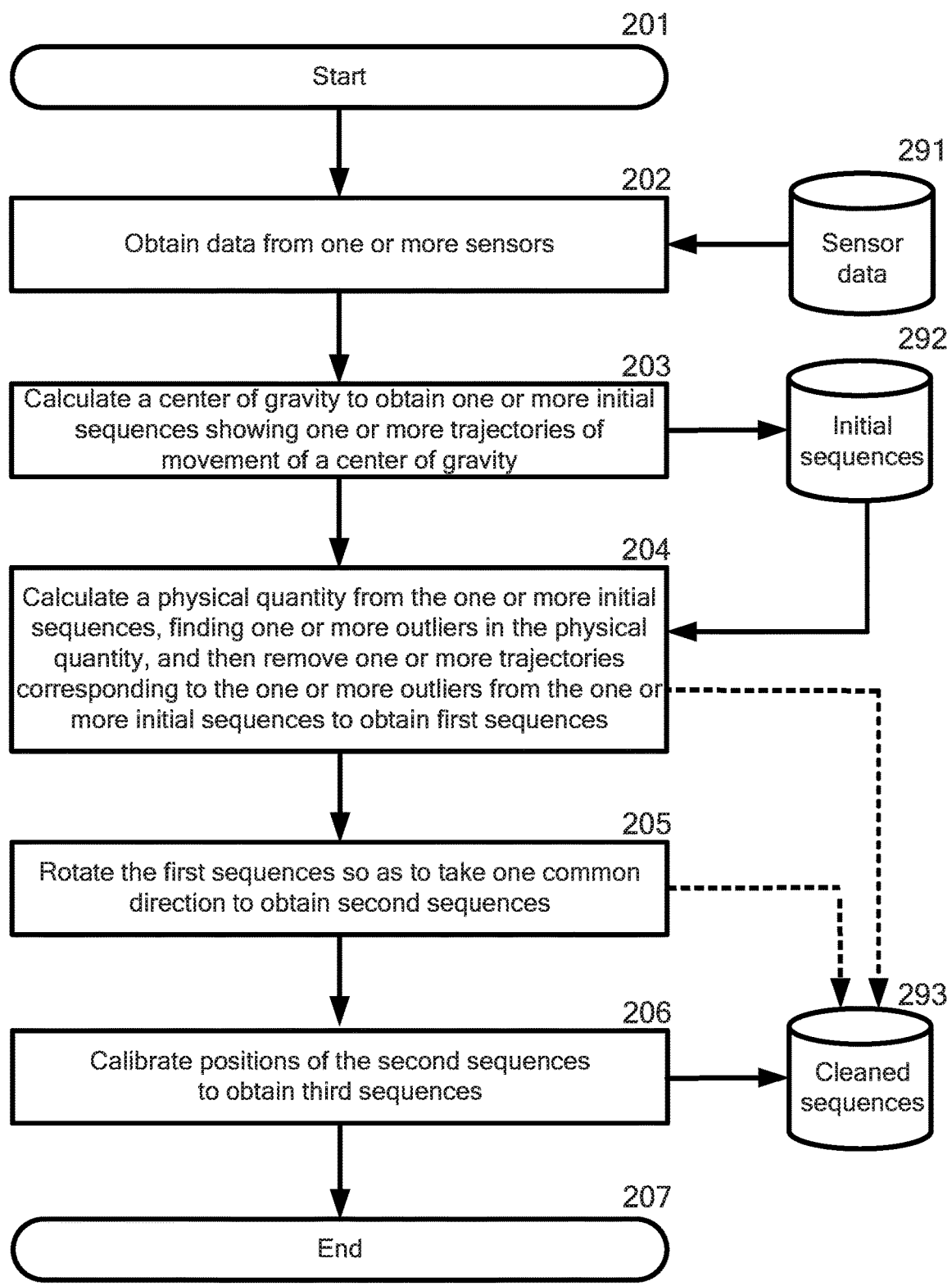
FIG. 2A illustrates an embodiment of a flowchart of a process for obtaining cleaned sequences showing trajectories of movement of a center of gravity.
Figure 2B:
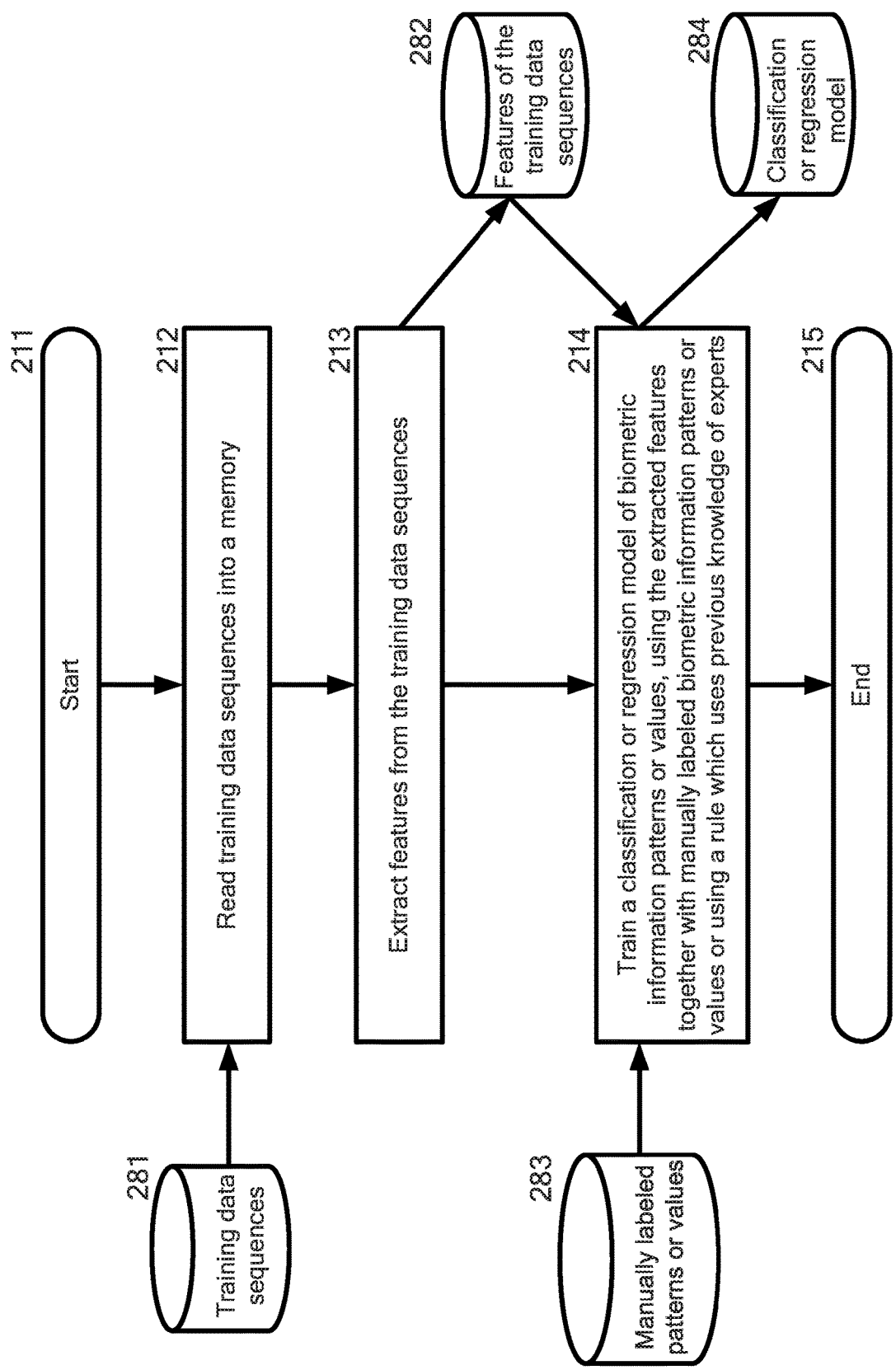
FIG. 2B illustrates an embodiment of a flowchart of a process for training a classification or regression model of biometric information patterns or values.
Figure 2C:
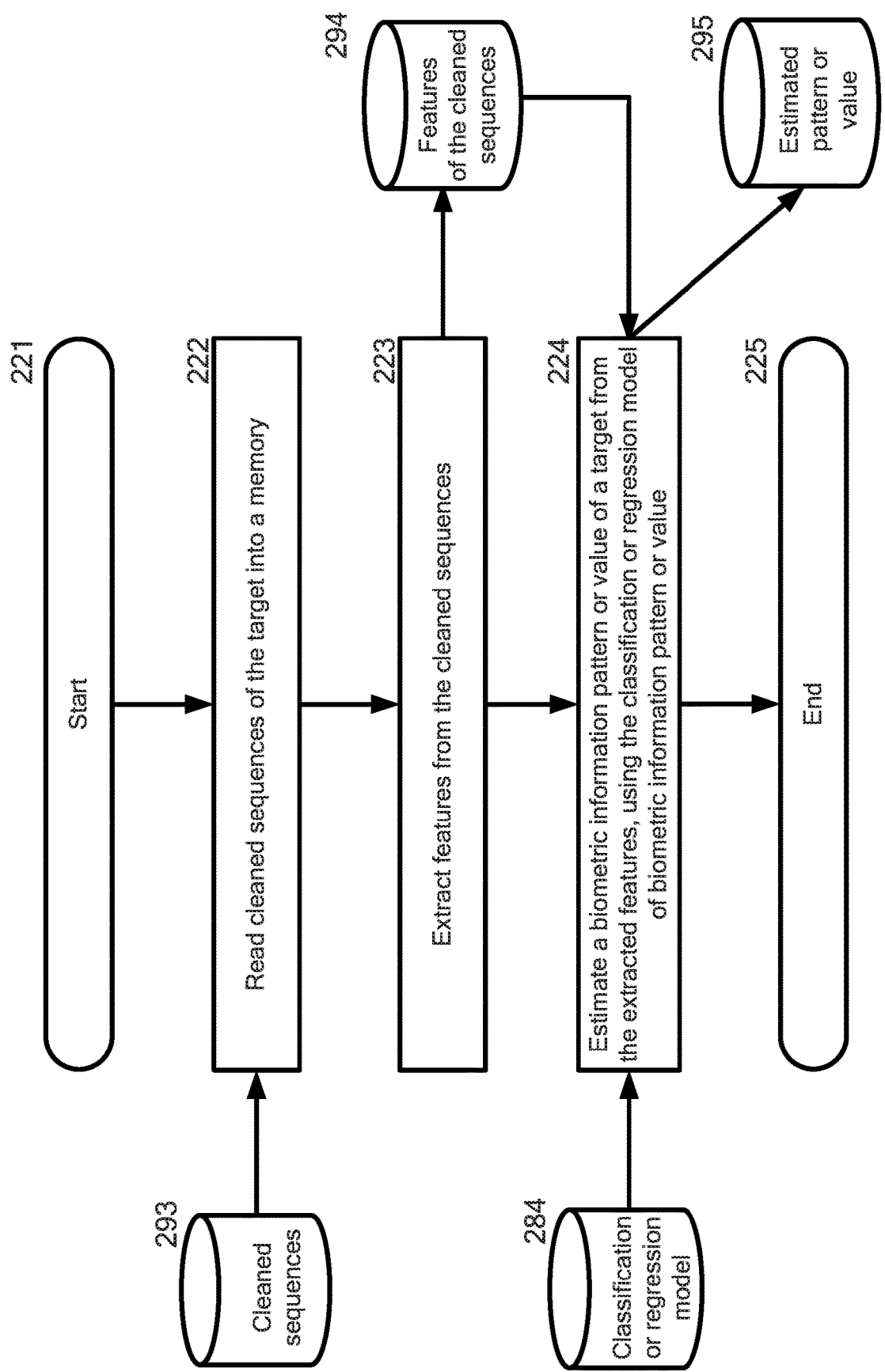
FIG. 2C illustrates an embodiment of a flowchart of a process for estimating a biometric information pattern or value of a target.

FIGS. 2A to 2C illustrate flowcharts of a process according to an embodiment of the present invention.

With reference now to FIG. 3A, FIG. 3A illustrates an embodiment of a flowchart of a process for obtaining cleaned sequences showing trajectories of movement of a center of gravity.

The aim of the process mentioned above is to obtain the cleaned sequences which represent a pattern derived from respiratory or circulatory organs of a target.

Let us suppose that a target, such as a human or an animal, is now is lying, sleeping or sitting on a bed or chair.

The term, "a human", may include any person, for example, but not limited to, a healthy person, a person who needs nursing care and patient.

The term, "an animal", may include any animal, for example, but not limited to, a companion animal, domestic animal, race animal and zoo animal. The animals may be, for example, but not limited to, a healthy animal, an animal that needs nursing care and an animal in an animal hospital.

The term, "a bed", may include any type of beds, for example, but not limited to, medical treatment beds, nursing beds and furniture beds.

The term, "a chair", may include any type of chairs, for example, but not limited to, medical treatment chairs, nursing chairs and furniture chairs.

A system, such as the computer (101), may perform each step described in FIG. 2A. The system may be implemented as a single computer or plural computers.

In step 201, the system starts the process mentioned above.

In step 202, the system reads data obtained from one or more sensors. The data may be read from a storage (291) where the data obtained from the one or more sensors is stored. Alternatively, the data may be directly or indirectly transmitted from each of the one or more sensors.

A sensor used according to an embodiment of the present invention may be any sensor which can measure data for calculating one or more initial sequences showing one or more trajectories of movement of a center of gravity. The sensor may be one or more load sensors, one or more visual sensors, one or more infrared sensors or combination of these. A combination of different types of sensors can be used.

The load sensor may refer to a transducer which converts an input mechanical force into an electrical output signal. The load sensors are also commercially known as load transducers or load cells. Any load sensor commercially available can be used for an embodiment of the present invention. One embodiment of a usage of load sensors will be described below by referring to FIG. 3.

The visual sensor may refer to a motion sensing input device, for example, but not limited to, a web camera. Any visual sensor commercially available can be used for an embodiment of the present invention.

The infrared sensor may refer to an electronic sensor that measures infrared light radiating from object in its field of view, for example, but not limited to, Kinect™ sensor from Microsoft® Corporation. Any infrared sensor commercially available can be used for an embodiment of the present invention.

The sensor may be tuned to effectively take desired biometric information, such as information relating to respiratory or circulatory organs in advance.

In step 203, the system calculates a center of gravity, based on data obtained from the one or more sensors, to obtain one or more initial sequences showing one or more trajectories of movement of a center of gravity. Any method known to the art can be used for calculating a center of gravity, based on data obtained from the one or more sensors.

When data obtained from the load sensor is used, a center of gravity may be a physical center of gravity. When obtained data from the visual sensor or infrared sensor is used, a center of gravity may be a geometric center of gravity on a two or three-dimensional space.

The system may store the calculated initial sequence into a storage (292), such as a disk (108) described in FIG. 1.

In step 204, the system may remove one or more noises from the one or more initial sequences. The removal of one or more noises comprises removing, from the one or more initial sequence, one or more noises which are not one or more trajectories of movement of a center of gravity. The one or more noises may be derived from, for example, an influence of a body motion of a target. Accordingly, each noise may not be a trajectory relating to a biometric information pattern or value which is repeated at regular intervals.

The biometric information pattern may be, for example, but not limited to, a pattern derived from respiratory or circulatory organs of a target.

The respiratory organs may be any organ involved in the process of respiration, such as lungs, a bronchial tube, a pharynx or a mouse.

The circulatory organs may be any organ involved in the process of blood circulation, such as heart, blood vessel.

The pattern derived from respiratory organs of a target may be, for example, but not limited to, a pattern of a depth of respiration, a respiratory rate pattern, or a respiratory volume pattern; a snore pattern; or a pattern relating to a symptom of respiration related illness. The depth of respiration may include, for example, shallow respiration, normal respiration or deep respiration. The symptom of respiration related illness may be for example, but not limited to asthma, pneumonia, emphysema or apnea.

The pattern derived from circulatory organs of a target may be, for example, but not limited to, a cardiac rate pattern or a cardiac output pattern; a blood pressure pattern or a blood flow pattern; or a pattern relating to a symptom of heart or blood related illness. The symptom of heart or blood related illness may be for example, but not limited to heart disease such as coronary artery disease or heart rhythm problems, or blood vessel disease such as abnormal blood pressure.

The biometric information value may be, for example, but not limited to, value derived from respiratory or circulatory organs of a target.

The value derived from respiratory organs of a target may be, for example, but not limited to, an index value relating to a depth of respiration, a respiratory rate, or a respiratory volume; an index value relating to a snore; or an index value relating to a symptom of respiration related illness. The symptom of respiration related illness may be those mentioned above.

The value derived from circulatory organs of a target may be, for example, but not limited to, a cardiac rate value or a cardiac output value; a blood pressure value or a blood flow value; or a value relating to a symptom of heart or blood related illness. The symptom of heart or blood related illness may be those mentioned above.

An example of removing one or more noises from the one or more initial sequence is described as steps 204 and 205 mentioned below. In steps 204 and 205, one or more noises which are not one or more trajectories relating to biometric information, such as respiration or cardiac beat, are removed from the one or more initial sequences.

The system may remove one or more noises according to an embodiment of the following method (A), (B) or combination of these.

(A) The system may calculate a physical quantity from the one or more initial sequences, finding one or more outliers in the physical quantity, and then removing one or more trajectories corresponding to the one or more outliers from the one or more initial sequences to obtain first sequences.

(B) The system may estimate a probabilistic model for the physical quantity, finding one or more outliers which are the corresponding physical quantity of which the probability or probabilistic density is lower than predetermined threshold, and then removing one or more trajectories corresponding to the one or more outliers from the one or more initial sequences to obtain first sequences.

For the method (A) mentioned above, for example, the system can use the following physical quantity, (A-1), (A-2), or combination of these.

(A-1) The physical quantity may be a location of a center of gravity or a vector selected from the group consisting of a location vector of a center of gravity, a direction vector, a velocity vector, and an acceleration vector; or a combination of these.

If the physical quantity is a location of a center of gravity or a location vector of a center of gravity in (A-1) mentioned above, the system may find an abnormal location of the center of gravity when most of locations is within a predetermined range or find an abnormal location of the center of gravity based on a difference of statistic, such as standard deviation. After the abnormal location was found, the system removes one or more trajectories corresponding to the abnormal location of the center of gravity from the one or more initial sequences.

If the physical quantity is a direction vector, a velocity vector, and an acceleration vector in (A-1), the system may calculate one or more vectors from the one or more initial sequences. Any method known in the art can be used for calculating a direction vector, a velocity vector or an acceleration vector. For example, a velocity vector can be calculated as the difference vector between the center positions at time t and the center position at time t+1. The system may calculate, from direction vectors, a velocity vectors, and an acceleration vectors, one or more outliers as one or more direction outliers, one or more velocity outliers, and one or more acceleration outliers, respectively.

The system calculates a reference vector. The reference vector can be determined so as to minimize the distance from other velocity vectors. The system then classifies each center of gravity into a normal or abnormal velocity vector, based on the distance between the corresponding vector and the reference vector. The distance may be, for example, but not limited to, Euclid distance, cosine distance or L1-norm. The threshold used in the classification mentioned above can be determined manually or based on the mean of distance, such as constant multiplication of the mean. After the classification, the system separates trajectories in the one or more initial sequences normal or abnormal trajectories. For keeping the continuity, it is assumed that the minimum time width for trajectories is classified as normal. Finally, the system extracts normal trajectories which satisfy the time width mentioned above in order to remove abnormal trajectories from the one or more initial sequences.

(A-2) The physical quantity may be a vector or matrix which is selected from the group consisting of various statistics in a certain time window of a location of a center of gravity or a location vector of a center of gravity, a direction vector, a velocity vector, an acceleration vector or a combination of these. The static may be, for example, but not limited to an average, standard deviation, mean or quintiles.

If the physical quantity is a vector or matrix which is selected from the group consisting of various statistics in a certain time window of a location of a center of gravity or a location vector of a center of gravity, a direction vector, a velocity vector, an acceleration vector or a combination of these, for example, the system may calculate the vector or matrix and then find one or more amplitude outliers in the first sequences.

If the physical quantity is statistics in a certain time window of a location of a standard deviation in (A-2) mentioned above, for example the system may find amplitude outliers and then remove one or more trajectories corresponding to the one or more amplitude outliers from the first sequences. The example of finding amplitude outliers is as follows.

The system may separate the trajectories in the second sequences into a plurality of groups, using the sliding windows. The window size of the sliding window can be determined by, for example, manually or regular intervals of the biometric information, such as respiration intervals or cardiac beat intervals. The system then classifies abnormal groups based on corresponding statistical amount of the sequence in each window, using the prior knowledge that a proportion of normal groups are more than that of abnormal groups. For implementing this, implementations which are used for the removal of velocity outliers can be applied here. Abnormal trajectories, i.e. amplitude outliers, can be determined by a majority of result of the assignment of the trajectories in each window to the abnormal group.

For the method (B) mentioned above, the system can use, for example, but not limited to, the density estimation of particular model, such as Gaussian distribution, the Kernel density estimation, neural network, time-series models, or state space models, all of which are well known in the art.

In step 205, the system rotates the first sequences so as to take one common direction to obtain second sequences. For example, the system may rotate the first sequences, using the normal velocity vector corresponding to biometric information, such as respiration or cardiac beat, so as to take one common direction. This is because it is assumed that the direction of the normal velocity vector mentioned above may be the same to a direction of a vertical column of a human or animal. The normal velocity can be determined as mentioned above.

In step 206, the system calibrates positions of the second sequences to obtain third sequences. For example, the system may separate the trajectories in the second sequences into a plurality of groups, using the sliding windows. The window size of the sliding window can be determined by, for example, manually or regular intervals of the biometric information, such as respiration intervals or cardiac beat intervals. The system then calculates a reference position of each group. The reference position may be an average center position of the trajectories belonging to the group. The system then calculates a shift of each trajectory as average center position of the trajectories belonging to the group which is assigned a sliding window. Finally, the system calibrates positions of each trajectories based on the calculated shift.

The third sequences may be the cleaned sequences. The system may store the third sequences into a storage (293), such as a disk (108) described in FIG. 1.

In step 207, the system terminates the process mentioned above.

The step 202 to 203 can be omitted if the center of gravity was calculated by another computer which is different from the system mentioned above.

If there is no need to perform steps 205 and 206, the first sequences can be stored as the cleaned sequence into the storage (293).

If there is no need to perform step 205, the system may omit the step 205 and then calibrate positions of the first sequences to obtain third sequences as described in step 206.

If there is no need to perform step 206, the system may omit the step 206 and then store the second sequence as the cleaned sequence into the storage (293).

According to the embodiment of the process described in FIG. 2A, the one or more initial sequences which are calculated from a center of gravity can be obtained without burden of a target and, further, one or more noises which are not one or more trajectories relating to a biometric information pattern or value which is repeated at regular intervals can be removed from one or more initial sequences to obtain cleaned sequences.

With reference now to FIG. 2B, FIG. 2B illustrates an embodiment of a flowchart of a process for training a classification or regression model of biometric information patterns or values.

A system such as the computer (101) may perform each steps described in FIG. 2B. The system used in FIG. 2B may be the same or different from the system used in FIG. 2A. The system may be implemented as a single computer or plural computers.

In step 211, the system starts the process mentioned above.

In step 212, the system reads, into a memory such as a memory (103) described in FIG. 1, the training data sequences from a storage (281).

In step 213, the system extracts features from the training data sequences. For example, an average, a standard deviation, or quintiles can be used for extracting the features. The training data may be cleaned sequences obtained before. The feature may be, for example, but not limited to, standard deviation of a vertical position of the center of gravity.

The system may store the extracted features of the training data sequences into a storage (282), such as a disk (108) described in FIG. 1.

In step 214, the system reads, into a memory such as a memory (103) described in FIG. 1, manually labeled biometric information patterns or values from a storage (283) and then trains a classification or regression model of biometric information patterns or values, using the extracted features of the training data sequences together with the manually labeled biometric information patterns or values, based on, for example, but not limited to least squares method, or using a rule which uses previous knowledge of experts such as doctors.

The classification or regression model of biometric information patterns may be a classification or regression model of patterns derived from respiratory or circulatory organs. For example, generalized linear models may be used for the classification or regression model, and also, non-linear models, such as decision tree or regression tree, neural network, and kernel method, may be used for the classification or regression model.

If the classification or regression model of patterns derived from respiratory organs is required, the system may train a classification or regression model of patterns derived from respiratory organs, using the extracted features of the training data sequences together with manually labeled patterns or values, based on, for example, but not limited to least squares method, or using a rule which uses previous knowledge of experts.

If the classification or regression model of patterns derived from circulatory organs is required, the system may train a classification or regression model of patterns derived from circulatory organs, using the extracted features of the training data sequences together with manually labeled patterns or values, based on, for example, but not limited to least squares method, or using a rule which uses previous knowledge of experts.

The manually labeled biometric information pattern may be a pattern derived from respiratory or circulatory organs and the pattern is associated with a specified biometric pattern by an expert, such as a doctor. The label relating to respiratory organs may be, for example, but not limited to, a label of a depth of respiration, a respiratory rate or a respiratory volume; a label of a snore pattern; or a label of a symptom of respiration related illness. The label relating to circulatory organs may be, for example, but not limited to, a label of a cardiac rate or a cardiac output; a label of a blood pressure or a blood flow; or a label of a symptom of heart or blood related illness.

When the least squares method is used for training the classification or regression model of biometric information patterns or values, the classification or regression model is trained by evaluating degree of matching between the correct data and the classification or regression model, using the square error.

The system may store the classification or regression model of biometric information patterns or values into a storage (284), such as a disk (108) described in FIG. 1.

In step 215, the system terminates the process mentioned above.

According to the embodiment of the process described in FIG. 2B, a classification or regression model of biometric information patterns or values can be obtained, which is used for estimating a biometric information pattern or value of a target.

With reference now to FIG. 2C, FIG. 2C illustrates an embodiment of a flowchart of a process for estimating a biometric information pattern or value of a target.

A system such as the computer (101) may perform each steps described in FIG. 2C. The system used in FIG. 2C may be the same or different from the system used in FIG. 2A or FIG. 2B. The system may be implemented as a single computer or plural computers.

In step 221, the system starts the process mentioned above.

In step 222, the system reads, into a memory such as a memory (103) described in FIG. 1, the cleaned sequences of the target from the storage (293). For example, an average, a standard deviation, or quintiles can be used for extracting the features. The feature may be, for example, but not limited to, standard deviation of a vertical position of the center of gravity.

In step 223, the system extracts features of the target from the cleaned sequences. For example, an average, a standard deviation, or quintiles can be used for extracting the features.

The system may store the extracted features of the cleaned sequences into a storage (294), such as a disk (108) described in FIG. 1.

In step 224, the system may read, into a memory such as a memory (103) described in FIG. 1, the classification or regression model of biometric information patterns or values from the storage (284). The system then estimates a biometric information pattern or value of a target from the extracted features of the cleaned sequences, using the classification or regression model of biometric information patterns or values. As stated above, the biometric information pattern of a target may be, for example, but not limited to, a pattern derived from respiratory or circulatory organs of a target. As stated above, the biometric information value of a target may be, for example, but not limited to, value derived from respiratory or circulatory organs of a target. The system may store the estimated biometric information pattern or value of a target into a storage (295), such as a disk (108) described in FIG. 1.

In step 225, the system terminates the process mentioned above.

According to the embodiment of the process described in FIG. 2C, valuable features can be extracted from the cleaned sequence of a target. The extracted features of the cleaned sequences can be used for estimating a biometric information pattern or value of the target. Accordingly, the biometric information pattern or value of the target can be obtained, without any constraint and invasive treatment to the target.

Figure 3:
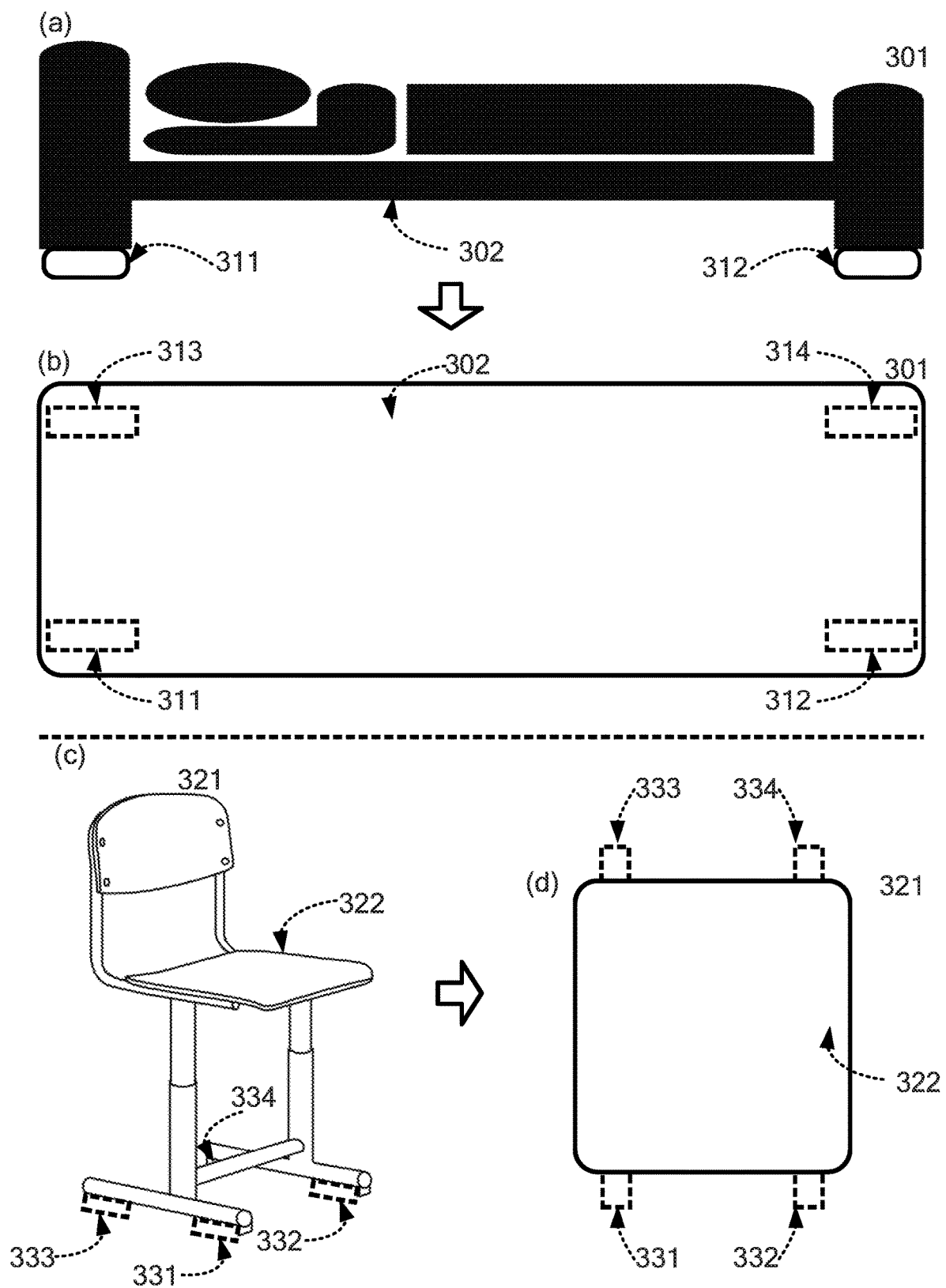
FIG. 3 illustrates an embodiment of load sensors attached to a bed or chair.

With reference now to FIG. 3, FIG. 3 illustrates an embodiment of load sensors attached to a bed (301) or chair (321).

Any load sensor commercially available can be used. In an embodiment of the present invention, plural load sensors are attached to a bed or chair. For example, plural load sensors may be mounted beneath legs of a bed or chair. The number of load sensors may be two or more, for example four. If the number of load sensors is four, each load sensor may be attached beneath each leg of a bed or chair.

The illustration (a) shows a side view of the bed (301). The illustration (b) shows a top view seen from directly above the bed (301). A human or animal can lie, sleep or sit on the bed (301).

Four load sensors (311, 312, 313 and 314) are mounted beneath each leg of a bed body (302) of the bed (301), respectively.

The illustration (c) shows a diagonal side view of the chair (321). The illustration (d) shows a top view seen from directly above the chair (321). A human or animal can sit, sleep or lie, on the chair (321).

Four load sensors (331, 332, 333 and 334) are mounted beneath each leg of a chair body (322) of the chair (321), respectively.

A system, such as a computer (101) described in FIG. 1, may receive data from the load sensors. Alternatively, a storage, such as a network attached storage (NAS), may receive data from the load sensors.

Load sensors attached to a bed or chair is promising method for non-intrusive sensing.

Figure 4:
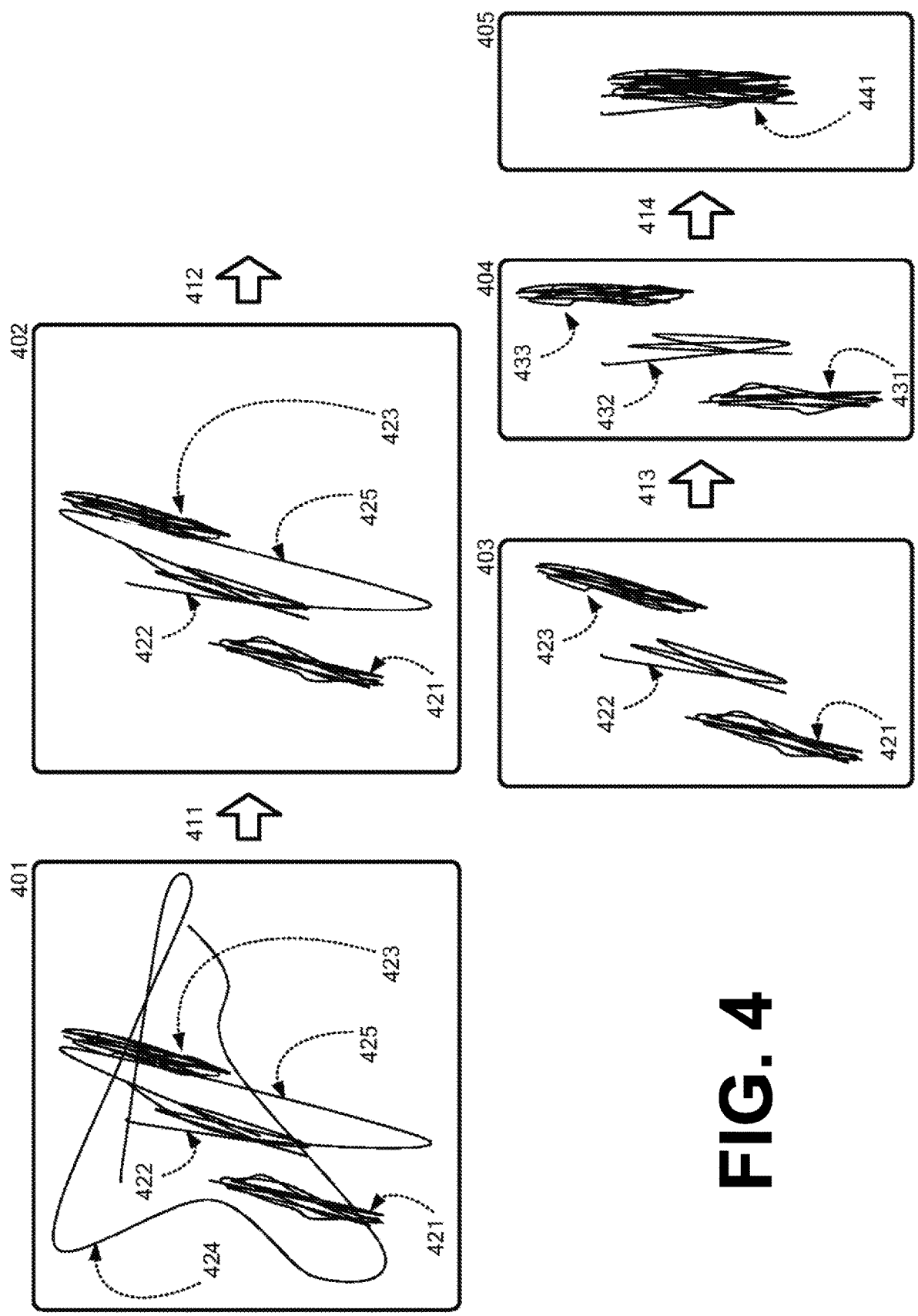
FIG. 4 illustrates an embodiment of obtaining cleaned sequences from one or more initial sequences.

With reference now to FIG. 4, FIG. 4 illustrates an embodiment of obtaining cleaned sequences from one or more initial sequences.

FIG. 4 shows how the initial sequences can be cleaned according to an embodiment of the flowchart described in FIG. 2A, by referring to the sequences (401 to 405).

The initial sequences (401) can be obtained according to step 203 described in FIG. 2A. The initial sequences (401) include trajectories (421, 422 and 423) and trajectories (424 and 425) of the initial sequences (401).

The system performs step 204 described in FIG. 2A.

The trajectories (424 and 425) will be judged as noises. That is, the trajectories (424 and 425) are not trajectories relating to a respiration pattern.

The trajectory (424) is judged as an abnormal movement of the center of gravity. Accordingly, the trajectory (424) is removed from the initial sequences (411), as shown in sequence 402.

Further, the trajectory (425) is judged as amplitude outliers. Accordingly, the trajectory (425) is further removed from the initial sequences (412).

After the removal of the trajectories (424 and 425), a first sequences (403) is obtained. The first sequences (403) includes trajectories (421, 422 and 423), which may relate to a respiration pattern.

The system performs step 205 described in FIG. 2A.

The system rotates the first sequences (403) so as to take one common direction to obtain second sequences (413). Thus, the trajectories (421, 422 and 423) in the first sequences (403) are rotated so as to take one common direction.

After the rotation of the first sequences (413), a second sequences (404) is obtained. The trajectories (431, 432 and 433) correspond to trajectories (421, 422 and 423) after the rotation, respectively.

The system performs step 206 described in FIG. 2A.

The system calibrates positions of the second sequences (404) so as to match centers of the trajectories (421, 422 and 423) with each other (414).

After the calibration of the second sequences (414), a third sequences (405) is obtained. The trajectories (441) include the trajectories (431, 432 and 433) and the trajectories (431, 432 and 433) are overlapped with each other at centers of the trajectories (421, 422 and 423) with each other.

The third sequences (405) can be used for training a classification or regression model or value of respiration patterns or estimating a respiration pattern or value of a target.

Figure 5A:
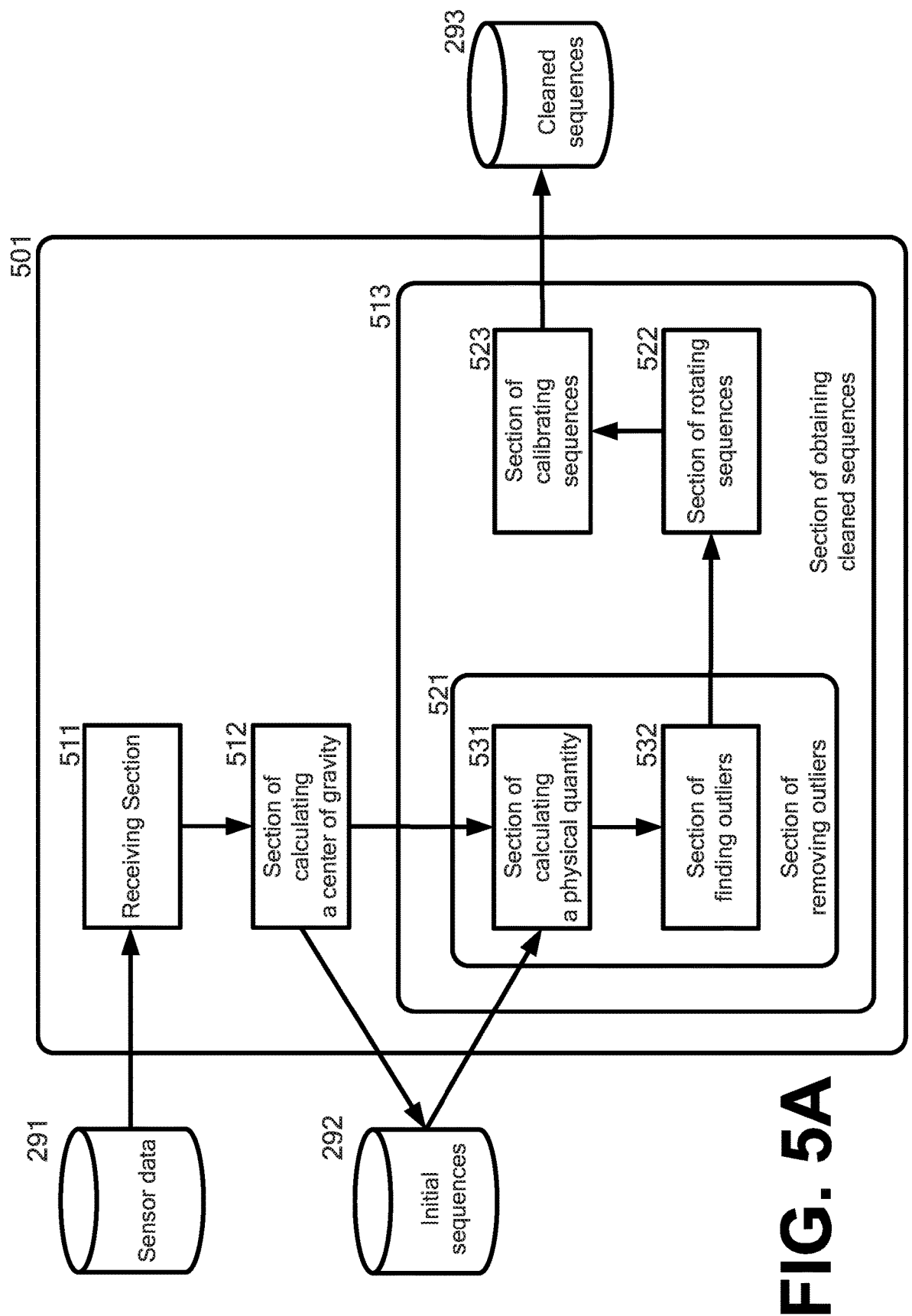
FIG. 5A illustrates an embodiment of an overall functional block diagram of a computer system hardware used in accordance with the embodiment of the flowchart described in FIG. 2A.
Figure 5B:
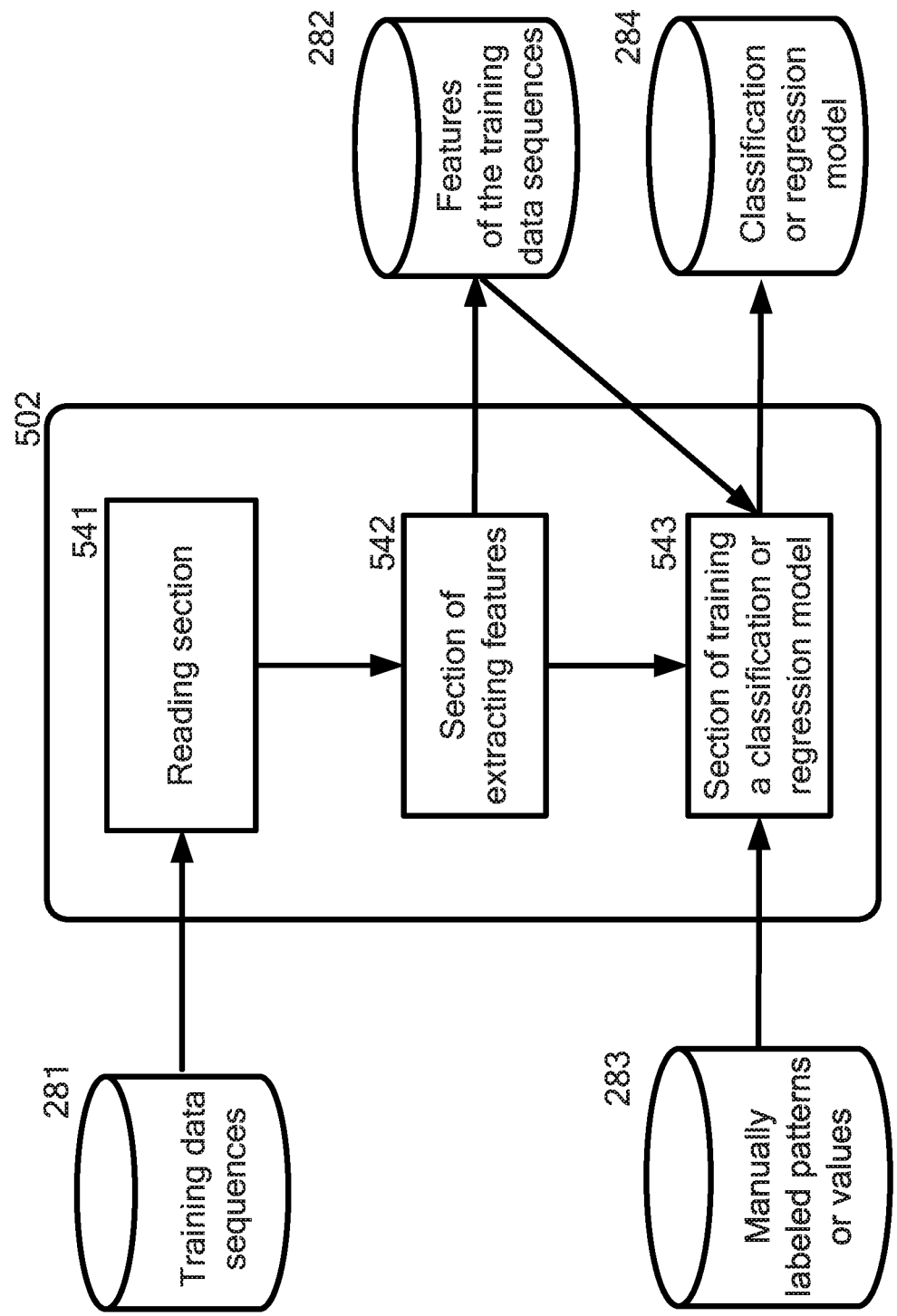
FIG. 5B illustrates an embodiment of an overall functional block diagram of a computer system hardware used in accordance with the embodiment of the flowchart described in FIG. 2B.
Figure 5C:
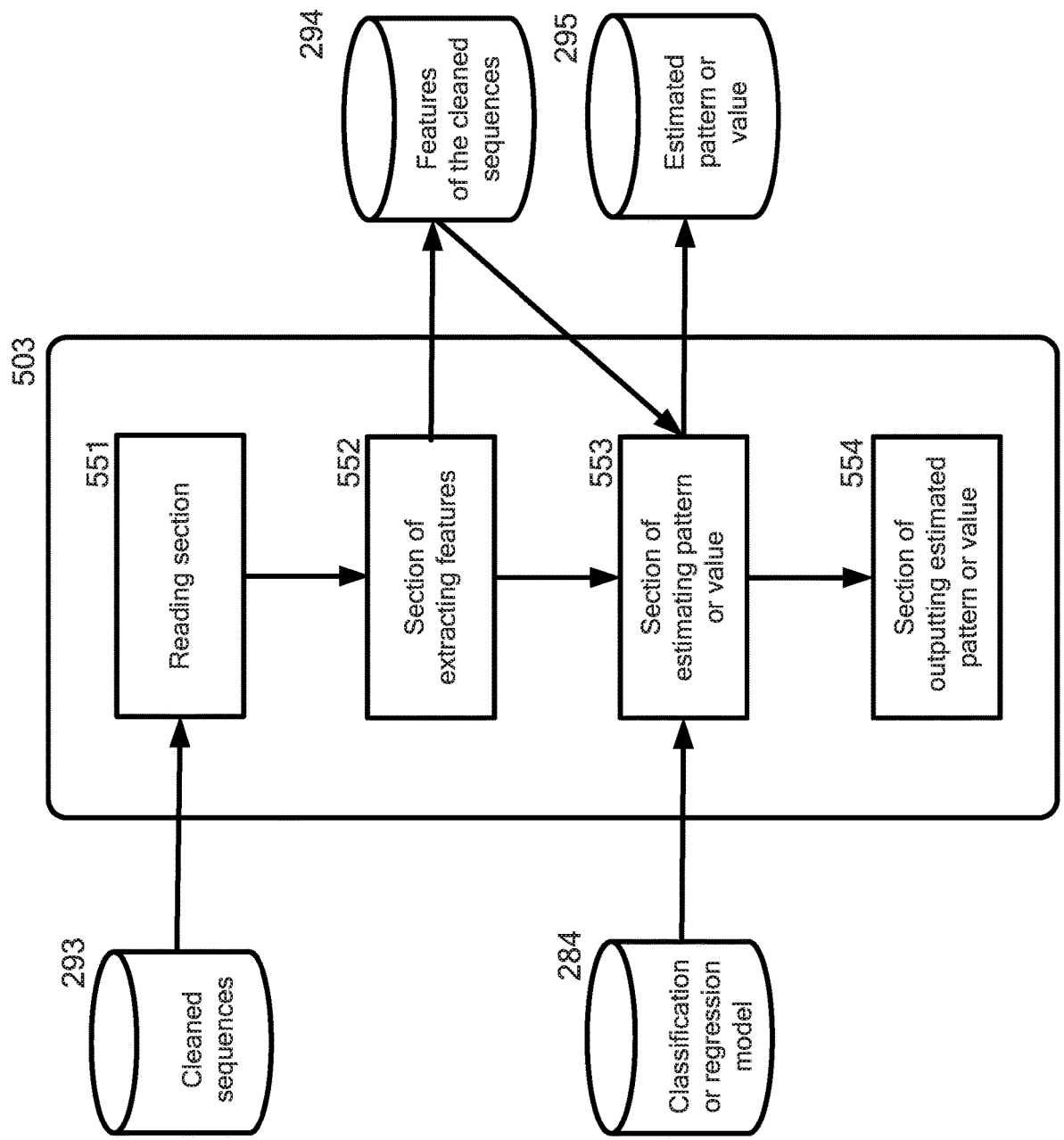
FIG. 5C illustrates an embodiment of an overall functional block diagram of a computer system hardware used in accordance with the embodiment of the flowchart described in FIG. 2C.

FIGS. 5A to 5C illustrate an overall functional block diagram of a computer system hardware in accordance with an embodiment of the present invention.

With reference now to FIG. 5A, FIG. 5A illustrates an embodiment of an overall functional block diagram of a computer system hardware used in accordance with the embodiment of the flowchart described in FIG. 2A.

The system (501) may correspond to the computer (101) described in FIG. 1.

The system (501) comprises a section of obtaining cleaned sequences (513). Further, the system (501) may optionally comprise a receiving section (511) and a section of calculating a center of gravity (512).

The receiving section (511) may perform step 202 described in FIG. 2A.

The section of calculating a center of gravity (512) may perform step 203 described in FIG. 2A.

The section of obtaining cleaned sequences (513) may remove one or more noises from one or more initial sequences The section of obtaining cleaned sequences (513) may receive the one or more initial sequences from the section of calculating a center of gravity (512). Alternatively, the section of obtaining cleaned sequences (513) may receive the one or more initial sequences from a storage (292) where the calculated initial sequence is stored.

The section of obtaining cleaned sequences (513) may comprise a section of removing outliers (521), a section of rotating sequences (522) and a section of calibrating sequences (523).

The section of removing outliers (521) may comprise a section of calculating a physical quantity (531) and a section of finding outliers (532).

The section of calculating a physical quantity (531) may calculate a physical quantity from the one or more initial sequences.

The section of finding outliers (532) may find one or more outliers in the physical quantity, and then removing one or more trajectories corresponding to the one or more outliers from the one or more initial sequences to obtain first sequences.

The section of rotating sequences (522) may perform step 205 described in FIG. 2A.

The section of calibrating sequences (523) may perform step 206 described in FIG. 2A.

With reference now to FIG. 5B, FIG. 5B illustrates an embodiment of an overall functional block diagram of a computer system hardware used in accordance with the embodiment of the flowchart described in FIG. 2B.

The system (502) may correspond to the computer (101) described in FIG. 1. The system (502) may be the same or different from the system (501) described in FIG. 2A.

The system (502) comprises a reading section (541), a section of extracting features (542) and a section of training a classification or regression model (543).

The reading section (541) may perform may perform step 212 described in FIG. 2B.

The section of extracting features (542) may perform step 213 described in FIG. 2B.

The section of training a classification or regression model (543) may perform step 214 described in FIG. 2C.

With reference now to FIG. 5C, FIG. 5C illustrates an embodiment of an overall functional block diagram of a computer system hardware used in accordance with the embodiment of the flowchart described in FIG. 2C.

The system (503) may correspond to the computer (101) described in FIG. 1. The system (503) may be the same or different from the system (501) described in FIG. 2A or the system (502) described in FIG. 2B.

The system (503) comprises a reading section (551), a section of extracting features (552), and a section of estimating pattern or value (553). The system (503) may further optionally comprise a section of outputting estimated pattern or value (554).

The reading section (551) may perform step 222 described in FIG. 2C.

The section of extracting features (552) may perform step 223 described in FIG. 2C.

The section of estimating pattern or value (553) may perform step 224 described in FIG. 2C.

The section of outputting estimated pattern or value (554) may output the estimated biometric information pattern or value of a target, or processed data calculated from the estimated biometric information pattern or value. The section of outputting estimated pattern or value (554) may display the estimated biometric information pattern or value of a target, or the processed data on a display device, such as the display (106) described in FIG. 1 or print the estimated biometric information pattern or value of a target, or the processed data.

The present invention may be a method, a system, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

By the expression "a/one" should be understood as "at least one".

By the expression "comprise(s)/comprising a/one" should be understood as "comprise(s)/comprising at least one".

By the expression "comprise(s)/comprising" should be understood as "comprise(s)/comprising at least".

By the expression "/" should be understood as "and/or".

What is claimed is:

1. A method for estimating biometric information, the method comprising:
   determining one or more data sequences showing one or more trajectories of movement of an individual based on sensor data from at least one non-intrusive sensor;
   selectively removing one or more noises from the one or more data sequences;
   rotating the one or more trajectories in the one or more data sequences to overlap a center of gravity; and
   estimating the biometric information from the one or more data sequences.

2. The method according to claim 1, wherein the biometric information is a biometric information pattern which is repeated at regular intervals.

3. The method according to claim 2, wherein the biometric information pattern is a pattern derived from respiratory or circulatory organs of the individual.

4. The method according to claim 1, wherein selectively removing one or more noises comprises removing, from the one or more data sequences, one or more noises which are not one or more trajectories relating to a biometric information pattern or value which is repeated at regular intervals.

5. The method according to claim 1, wherein the at least one sensor is selected from the group consisting of load sensors, visual sensors, and infrared sensors.

6. The method according to claim 5, wherein the at least one sensor includes a plurality of load sensors, and wherein the plurality of load sensors are attached to a bed or chair on which the individual is lying, sleeping or sitting.

7. The method according to claim 1, wherein selectively removing one or more noises is carried out by calculating a physical quantity from the one or more data sequences, finding one or more outliers in the physical quantity, and then removing one or more trajectories corresponding to the one or more outliers from the one or more data sequences to obtain first data sequences.

8. The method according to claim 7, wherein the physical quantity is a physical quantity selected from the group consisting of a location of a center of gravity or a location vector of a center of gravity, a direction vector, a velocity vector, and an acceleration vector.

9. The method according to claim 7, wherein the physical quantity is selected from the group consisting of various statistics in a certain time window of a location of a center of gravity or a location vector of a center of gravity, a direction vector, a velocity vector, and an acceleration vector.

10. The method according to claim 7, the one or more trajectories corresponding to the one or more outliers is one or more trajectories of abnormal movement of the center of gravity.

11. The method according to claim 7, wherein a probabilistic model for the physical quantity is estimated, the one or more outliers are corresponding physical quantities for which a probability or probabilistic density is lower than a predetermined threshold, and the removal of noises is carried out by removing one or more trajectories corresponding to the one or more outliers from the one or more data sequences.

12. The method according to claim 11, wherein the probabilistic model is estimated by a density estimation of a particular model, a Kernel density estimation, a neural network, time-series models, or state space models.

13. The method according to claim 7, wherein rotating the one or more trajectories in the one or more data sequences comprises rotating one or more data sequences to overlap a center of gravity to obtain second data sequences.

14. The method according to claim 13, the method further comprising calibrating positions of the second data sequences to obtain third data sequences.

15. A method for estimating a biometric information pattern or value of an individual, the method comprising:
reading, into a memory, data sequences of the individual obtained by the method according to claim 1, wherein selectively removing one or more noises is carried out by removing one or more noises which are not a trajectory relating to a biometric information pattern or value, wherein removing one or more noises is repeated at regular intervals;
extracting features from the data sequences; and
estimating a biometric information pattern or value of the individual from the extracted features, using a classification or regression model of biometric information patterns or values.

16. The method according to claim 15, wherein the classification or regression model of biometric information patterns or values is obtained by: reading training data sequences; extracting features from the training data sequences; and training the classification or regression model, using the features extracted from the training data sequences together with manually labeled biometric information patterns or values or using a rule which uses previous knowledge of experts.

17. A system, comprising:
a processor; and
a memory storing a program, which, when executed on the processor, performs an operation for estimating biometric information, the operation comprising:
determining one or more data sequences showing one or more trajectories of movement of an individual based on sensor data from at least one non-intrusive sensor;
selectively removing one or more noises from the one or more data sequences;
rotating the one or more trajectories in the one or more data sequences to overlap a center of gravity; and
estimating the biometric information from the one or more data sequences.

18. The system according to claim 17, wherein the removing one or more noises is carried out by calculating a physical quantity from the one or more data sequences, finding one or more outliers in the physical quantity, and then removing one or more trajectories corresponding to the one or more outliers from the one or more data sequences to obtain first data sequences.

19. A computer program product for estimating biometric information, the computer program product comprising a non-transitory computer readable storage medium having program instructions embodied therewith, the program instructions executable by a computer to cause the computer to perform a method comprising:
determining one or more data sequences showing one or more trajectories of movement of an individual based on sensor data from at least one non-intrusive sensor;
selectively removing one or more noises from the one or more data sequences;
rotating the one or more trajectories in the one or more data sequences to overlap a center of gravity; and
estimating the biometric information from the one or more data sequences.

20. The computer program product according to claim 19, wherein the removing one or more noises is carried out by calculating a physical quantity from the one or more data sequences, finding one or more outliers in the physical quantity, and then removing one or more trajectories corresponding to the one or more outliers from the one or more data sequences to obtain first data sequences.

* * * * *